United States Patent
Steele et al.

[11] Patent Number: 5,939,244
[45] Date of Patent: Aug. 17, 1999

[54] PHOTOGRAPHIC COUPLER AND ELEMENT

[75] Inventors: David A. Steele, Webster; Jerrold N. Poslusny, Rochester; Paul B. Merkel, Victor, all of N.Y.

[73] Assignee: Eastman Kodak Company, Rochester, N.Y.

[21] Appl. No.: 08/938,000

[22] Filed: Sep. 26, 1997

[51] Int. Cl.$^6$ .............................. G03C 1/08; G03C 7/26; G03C 7/32
[52] U.S. Cl. .......................... 430/557; 430/543; 430/556
[58] Field of Search ..................................... 430/543, 557, 430/556

[56] References Cited

U.S. PATENT DOCUMENTS

| | | | |
|---|---|---|---|
| 2,298,443 | 10/1942 | Weissberger | 430/556 |
| 2,407,210 | 9/1946 | Weissberger et al. | 430/556 |
| 2,875,057 | 3/1959 | McCrossen et al. | 430/556 |
| 3,048,194 | 8/1962 | Weissberger et al. | 430/556 |
| 3,265,506 | 8/1966 | Weissberger et al. | 430/556 |
| 3,447,928 | 6/1969 | Loria | 430/556 |
| 4,106,942 | 8/1978 | Tanaka et al. | 430/557 |

FOREIGN PATENT DOCUMENTS 2-006947  6/1988  Japan.

OTHER PUBLICATIONS

Abstract—JP 02006947.

*Primary Examiner*—Geraldine Letscher
*Attorney, Agent, or Firm*—Andrew J. Anderson

[57] ABSTRACT

The invention provides a photographic yellow image dye-forming coupler represented by Formula I:

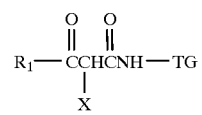

wherein $R_1$ is a substituent group; TG is a thiophene group; and X is hydrogen or a coupling-off group. The invention also provides a photographic element comprising a silver halide emulsion layer having associated therewith a dye-forming coupler of Formula I, as well as a process for forming an image in such a photographic element.

20 Claims, No Drawings

PHOTOGRAPHIC COUPLER AND ELEMENT

FIELD OF THE INVENTION

This invention relates to yellow dye-forming couplers, and more particularly to acylacetamido yellow dye forming couplers containing a thiophene group, as well as to silver halide photographic elements containing such couplers and processes for use of such elements.

BACKGROUND OF THE INVENTION

Conventional color photography depends on the imagewise formation of dyes and uses subtractive primaries to form the desired colors. Yellow, magenta, and cyan dyes are conventionally formed during photographic processing from dye-forming coupler compounds upon reaction with oxidized color developer. Each dye-forming coupler desirably provides good reactivity, while the formed dye desirably exhibits good stability. One of the typical problems encountered with many dyes formed from coupler compounds, e.g., is their tendency to degrade when exposed to light. This is of particular importance with respect to photographic elements intended for direct or projection viewing. Such elements include reflective prints and color transmission elements such as motion picture prints and projection slides. Such elements receive substantial exposure to light while being viewed. This not only causes the dye images to fade, but when the dyes of different colors fade at different rates, the image changes color and the neutral areas become undesirably colored.

Since the advent of color photography there have been ongoing efforts to provide yellow dye-forming couplers with improved properties, including reactivity, formed dye hue and dye stability. Typical yellow image dye-forming couplers are described in such representative patents and publications as: U.S. Pat. Nos. 2,875,057; 2,407,210; 3,265,506; 2,298,443; 3,048,194; 3,447,928 and "Farbkuppler - Eine Literature Ubersicht," published in Agfa Mitteilungen, Band III, pp. 112–126 (1961). Such couplers are typically open chain ketomethylene compounds. Frequently, yellow coupler compounds may provide advantageous results with respect to one property, while less than desired results with respect to others. Accordingly, it would be desirable to provide a new class of yellow image dye-forming couplers, especially a new class of such couplers which provides an advantageous combination of such properties.

Thus it is an object of the invention to provide a new class of yellow dye-forming coupler that exhibits good reactivity during photographic processing, as well as forming a dye having good resistance to light degradation.

SUMMARY OF THE INVENTION

The invention provides a photographic yellow image dye-forming coupler represented by Formula I:

$$R_1-\overset{O}{\overset{\|}{C}}CH\overset{O}{\overset{\|}{C}}NH-TG$$
$$\underset{X}{|}$$

I wherein $R_1$ is a substituent group; TG is a thiophene group; and X is hydrogen or a coupling-off group.

The invention also provides a photographic element comprising a silver halide emulsion layer having associated therewith a dye-forming coupler of Formula I, as well as a process for forming an image in such a photographic element.

DETAILED DESCRIPTION OF THE INVENTION

The invention provides photographic couplers represented by Formula I which form yellow image dyes upon reaction with oxidized color developing agents. $R_1$ is preferably an alkyl (including cycloalkyl and bridged cycloalkyl), aryl, anilino, alkylamino, arylamino or heterocyclic group. Representative $R_1$ groups include but are not limited to:

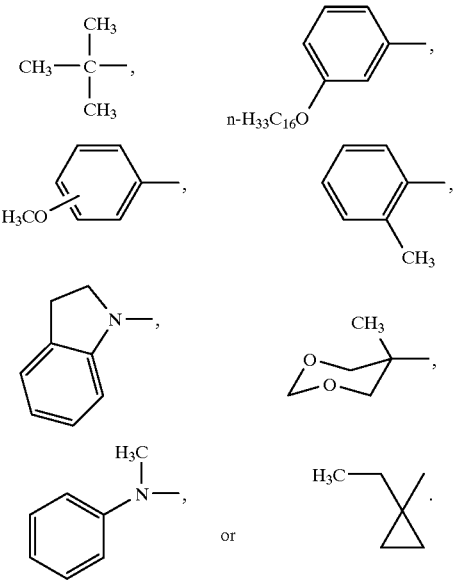

In particularly preferred embodiments of the invention $R_1$ is a tertiary alkyl group, most preferably a t-butyl group.

X is a hydrogen or a coupling-off group. Coupling-off groups are generally organic groups which are released during photographic processing. The released coupling-off group can be a photographically useful group.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

Generally the presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169; 3,227,551; 3,432,521; 3,476,563; 3,617, 291; 3,880,661; 4,052,212; and 4,134,766; and in U.K. Patents and published application Nos. 1,466,728, 1,531, 927, 1,533,039, 2,006,755A and 2,017,704A, the disclosures of which are incorporated herein by reference.

TG is preferably a substituted thiophene group wherein at least one substituent is a halogen atom or an alkoxy or aryloxy group. TG preferably additionally contains a ballasting group. Ballasting groups usually comprise one or more 5 to 25 carbon-atom-containing organic moieties whose function is to immobilize the coupler and the formed image dye during photographic development by imparting poor water diffusibility to the coupler compound.

The $R_1$, TG and X groups of Formula I may each contain further photographically acceptable substituents.

Yellow dye-forming couplers in accordance with one preferred embodiment of the invention include couplers of the formula II:

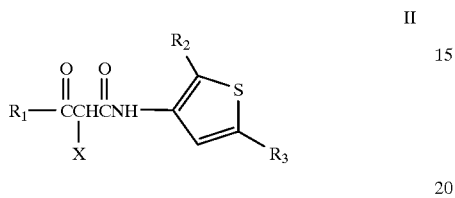

wherein $R_1$ and X are as described above, $R_2$ is an alkoxy or aryloxy group or a halogen atom, and $R_3$ is an electron withdrawing group. Electron withdrawing substituents are discussed in J. March, Advanced Organic Chemistry, pages 20–21, 228–229, 386–387, 494–497. In particular, preferred electron withdrawing substituents would have a Hammett $\sigma_p$ constant of greater than 0.1 and preferably between 0.1 and 1.0 (for example, between any of 0.3, 0.4, 0.5 or 0.6 and 1.0). Hammett $\sigma_p$ values are discussed in Advanced Organic Chemistry 3rd Ed., J. March, (John Wiley Sons, N.Y.; 1985). Note that the "p" subscript refers to the fact that the $\sigma$ values are measured with the substituents in the para position of a benzene ring. Additional tables relating to Hammett $\sigma_p$ constants can be found in Chemical Reviews Volume 91, pages 165–195 (authored by C. Hansch et al.). Examples of suitable electron withdrawing groups are a cyano group, substituted or unsubstituted carbamoyl groups having from 1 to 30 carbon atoms, such as methylcarbamoyl, ethylcarbamoyl, 4-methoxy-phenylcarbamoyl, N-methyl-N-octadecylcarbamoyl, 3-(2,4-di-pentylphenoxy)propylcarbamoyl, pyrrolidinocarbonyl, hexadecylcarbamoyl and di-n-octyl-carbamoyl groups, substituted or unsubstituted sulfamoyl groups having from 1 to 30 carbon atoms, such as methylsulfamoyl, diethylsulfamoyl, 3-(2,4-di-t-pentyl-phenoxy)propylcarbamoyl, phenylsulfamoyl, pyrrolidinosulfonyl and morpholinosulfonyl groups, substituted or unsubstituted alkoxycarbonyl groups having from 1 to 30 carbon atoms, such as methoxycarbonyl, ethoxycarbonyl, phenoxycarbonyl, 2-methoxyethoxycarbonyl, and hexadecyloxycarbonyl groups, substituted or unsubstituted sulfonyl groups having from 1 to 30 carbon atoms, such as methanesulfonyl, 4-methyl-phenylsulfonyl and dodecylsulfonyl groups, substituted or unsubstituted acyloxy groups having from 1 to 30 carbon atoms, such as dodecanoyloxy, a trifluoromethyl group, substituted or unsubstituted heterocyclic residues having from 1 to 30 carbon atoms, such as benzoxazole-2-yl and 5,5-dimethyl-2-oxazoline-2-yl groups, as described in U.S. Pat. No. 4,740,453, and others readily apparent to one skilled in the art. Preferred electron withdrawing groups for substituent $R_3$ include sulfamoyl, carbamoyl and sulfonyl groups.

Preferably, at least one of $R_1$, $R_2$ and $R_3$ comprises at least 5 Carbon atoms to provide an effective ballast function.

Representative yellow dye forming couplers in accordance with the invention include the following four-equivalent couplers YC1 through YC14:

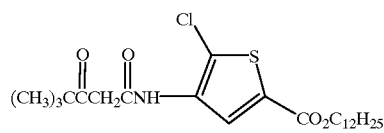

YC1

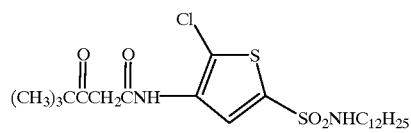

YC2

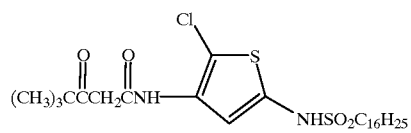

YC3

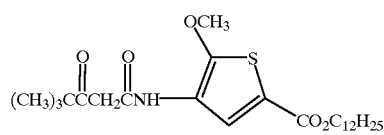

YC4

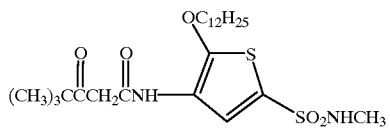

YC5

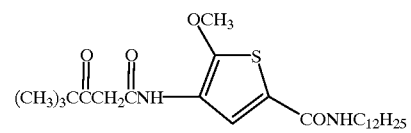

YC6

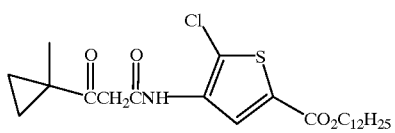

YC7

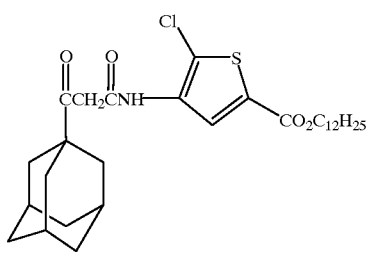

YC8

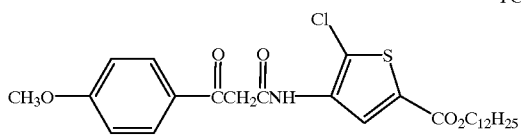

YC9

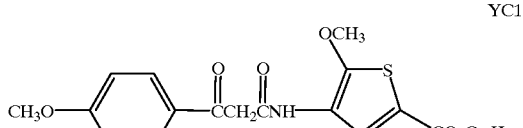

YC10

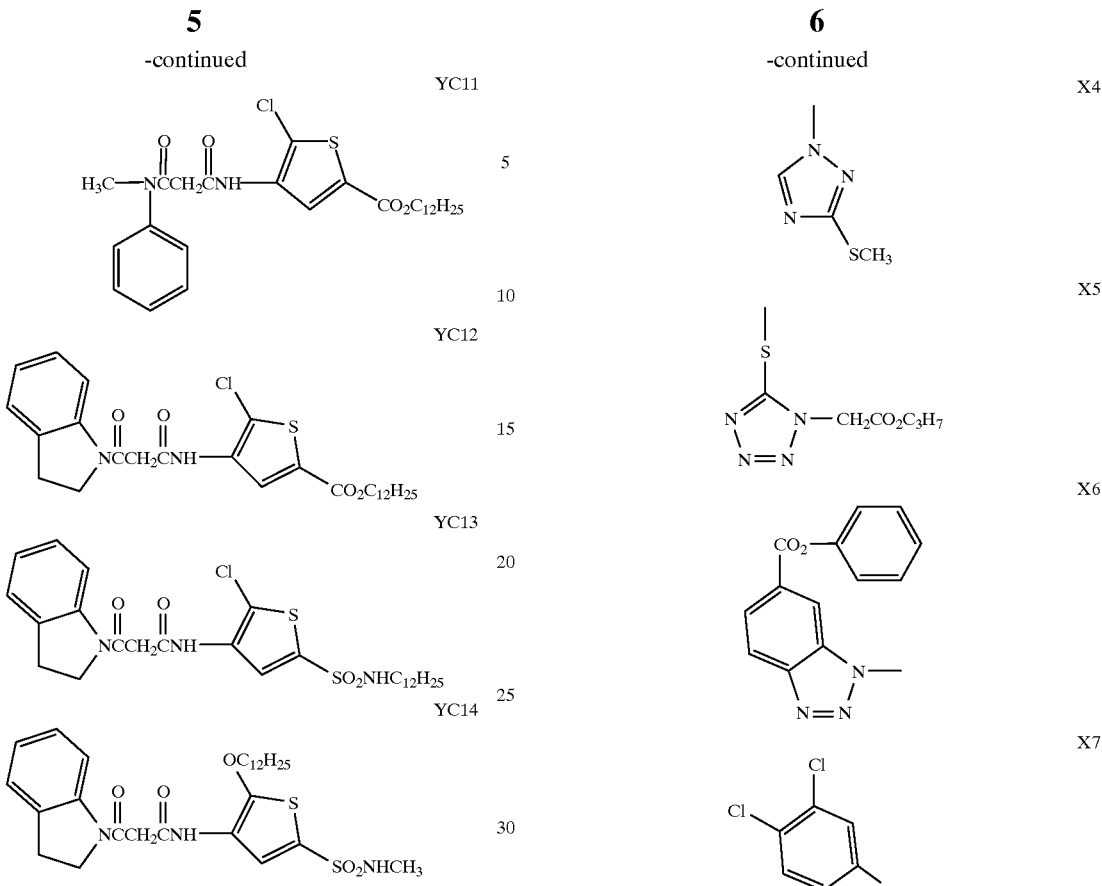

Representative two-equivalent couplers in accordance with the invention may be made, e.g., by substituting a coupling off group for a Hydrogen atom at the coupling-off position (i.e., as substitutent X in the above general formulas) in any of the above four-equivalent couplers. Preferred coupling-off groups for use in the couplers of the invention include halogen atoms such as Chloro and the following groups X1 through X10:

Examples of Coupling Off Groups (COGs)

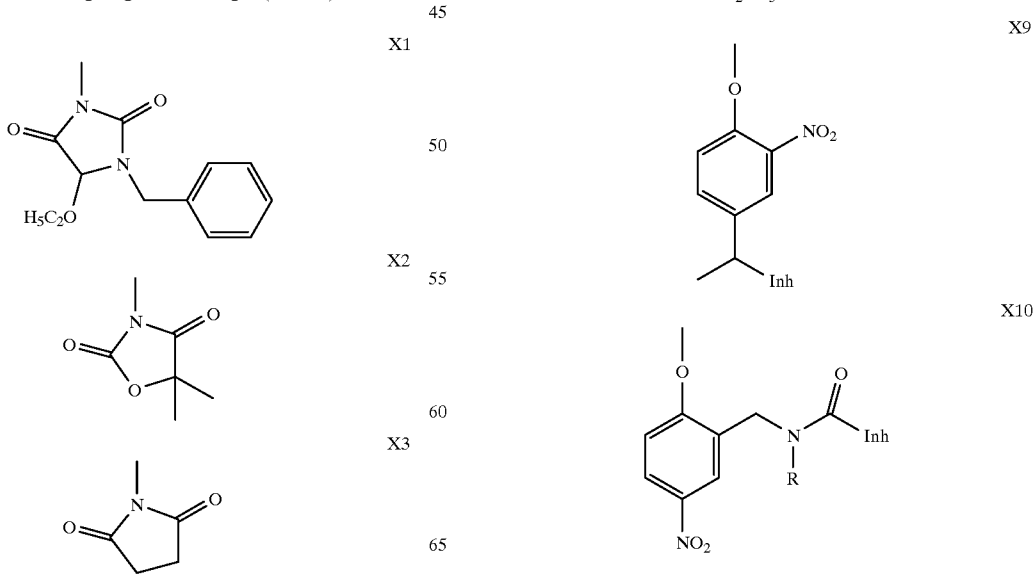

where Inh represents a photographic inhibitor moiety such as X5 above or as more fully described for DIR and DIAR couplers below and R represents an alkyl group.

Particularly preferred coupler in accordance with the invention include the following couplers YC1-X2, YC2-X1, and YC2-X2:

YC1-X2

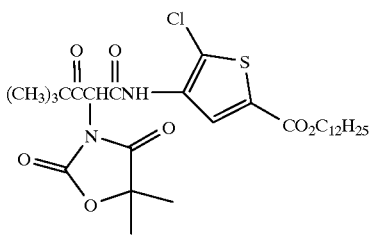

YC2-X1

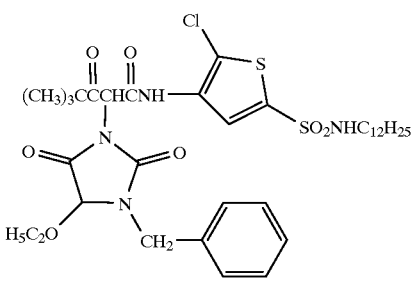

YC2-X2

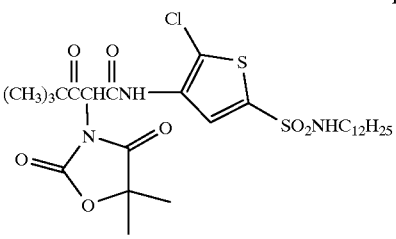

Couplers in accordance with the invention may be incorporated into a photographic element in accordance with any conventional technique. Typically, the couplers will be dispersed in a blue-light sensitive layer of a photographic element in a high boiling organic compound known in the art as a coupler solvent. Representative coupler solvents include phthalic acid alkyl esters such as diundecyl phthalate, dibutyl phthalate, bis-2-ethylhexyl phthalate, and dioctyl phthalate, phosphoric acid esters such as tricresyl phosphate, diphenyl phosphate, tris-2-ethylhexyl phosphate, and tris-3,5,5-trimethylhexyl phosphate, citric acid esters such as tributyl acetylcitrate, 2-(2-butoxyethoxy)ethyl acetate, and 1,4-cyclohexyldimethylene bis(2-ethylhexanoate), benzoic acid esters such as octyl benzoate, aliphatic amides such as N,N-diethyl lauramide, N,N-diethyldodecanamide, N,N-dibutyldodecanamide, mono and polyvalent alcohols such as oleyl alcohol and glycerin monooleate, and alkyl phenols such as p-dodecyl phenol and 2,4-di-t-butyl or 2,4-di-t-pentyl phenol. Commonly used coupler solvents are the phthalate esters, which can be used alone or in combination with one another or with other coupler solvents. Selection of the particular coupler solvent has been found to have an influence both on the activity of the coupler and the hue of the dye formed on coupling.

Unless otherwise specifically stated, substituent groups which may be substituted on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain allyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy- 3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4di-t-butylphenoxycarbonylamino, phenylcarbonylamino, 2,5-(di-t-pentylphenyl)carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3- to 7-membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in coupler molecules. Representative ballast groups include substituted or unsubstituted alkyl or aryl groups containing 8 to 42 carbon atoms. Representative substituents on such groups include alkyl, aryl, alkoxy, aryloxy, alkylthio, hydroxy, halogen, alkoxycarbonyl, aryloxycarbonyl, carboxy, acyl, acyloxy, amino, anilino, carbonamido, carbamoyl, alkylsulfonyl, arysulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1996, Item 38957, available as described above, which will be identified hereafter by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XII. Scan facilitating is described in Section XIV. Supports, exposure, development systems, and processing methods and agents are described in Sections XV to XX. Certain desirable photographic elements and processing steps are described in *Research Disclosure*, Item 37038, February 1995, and desirable features for color prints are described in *Research Disclosure*, Item 18716, November 1979.

The yellow dye forming couplers of the invention may be used in photographic elements in combination with any other desired photographic couplers, and will typically be used in combination with cyan and magenta dye-forming couplers, and optionally additional yellow dye-forming couplers.

Typical image dye-forming couplers that form cyan dyes upon reaction with oxidized color developing agents which are described in such representative patents and publications as: U.S. Pat. Nos. 2,367,531, 2,423,730, 2,474,293, 2,772, 162, 2,895,826, 3,002,836, 3,034,892, 3,041,236, 4,333,999, 4,883,746 and "Farbkuppler-eine LiteraturUbersicht," published in Agfa Mitteilungen, Band III, pp. 156–175 (1961).

Preferably such couplers are phenols and naphthols that form cyan dyes on reaction with oxidized color developing agent Couplers that form magenta dyes upon reaction with oxidized color developing agent are described in such representative patents and publications as: U.S. Pat. Nos. 2,311,082, 2,343,703, 2,369,489, 2,600,788, 2,908,573, 3,062,653, 3,152,896, 3,519,429, 3,758,309, 4,540,654, and "Farbkuppler-eine LiteratureUbersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidized color developing agents.

Couplers that form yellow dyes upon reaction with oxidized and color developing agent are described in such representative patents and publications as: U.S. Pat. Nos. 2,298,443, 2,407,210, 2,875,057, 3,048,194, 3,265,506, 3,447,928, 4,022,620, 4,443,536, and "Farbkuppler-eine LiteratureUbersicht," published in Agfa Mitteilungen, Band III, pp. 112–126 (1961). Such couplers are typically open chain ketomethylene compounds.

Couplers that form colorless products upon reaction with oxidized color developing agent may also be used in combination with the couplers of the invention. Such couplers are described in such representative patents as: U.K. Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent may also be used in combination with the couplers of the invention. Such couplers are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be used in combination with the couplers of the invention. These couplers do not contribute to image dye-formation. Thus, for example, a naphthol having an unsubstituted carbamoyl or one substituted with a low molecular weight substituent at the 2- or 3- position may be employed. Couplers of this type are described, for example, in U.S. Pat. Nos. 5,026,628, 5,151,343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629.

The invention materials may be used in association with materials that accelerate or otherwise modify the processing steps e.g. of bleaching or fixing to improve the quality of the image. Bleach accelerator releasing couplers such as those described in EP 193,389; EP 301,477; U.S. Pat. No. 4,163,669; U.S. Pat. No. 4,865,956; and U.S. Pat. No. 4,923,784, may be useful. Also contemplated is use of the compositions in association with nucleating agents, development accelerators or their precursors (UK Patent 2,097,140; U.K. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the compositions may be blocked or coated in protected form as described, for example, in Japanese Application 61/258,249 or U.S. Pat. No. 5,019,492.

The invention materials may further be used in combination with image-modifying compounds such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

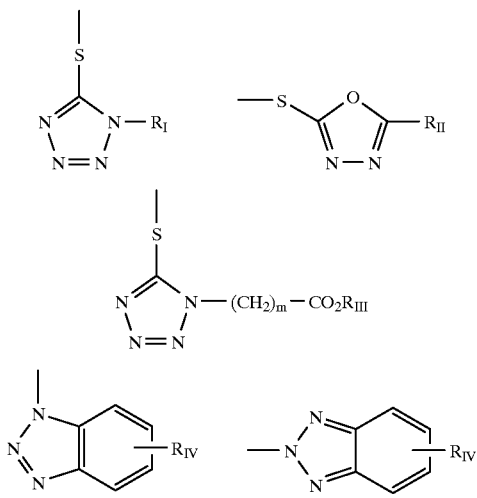

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group which produces the time-delayed release of the inhibitor group such as groups utilizing the cleavage reaction of a hemiacetal (U.S. Pat. No. 4,146,396, Japanese Applications 60-249148; 60249149); groups using an intramolecular nucleophilic substitution reaction (U.S. Pat. No. 4,248,962); groups utilizing an electron transfer reaction along a conjugated system (U.S. Pat. Nos. 4,409,323; 4,421,845; Japanese Applications 57-188035; 58-98728; 58-209736; 58-209738) groups utilizing ester hydrolysis (German Patent Application (OLS) No. 2,626,315; groups utilizing the cleavage of imino ketals (U.S. Pat. No. 4,546,073); groups that function as a coupler or reducing agent after the coupler reaction (U.S. Pat. No. 4,438,193; U.S. Pat. No. 4,618,571) and groups that combine the features describe above. It is typical that the timing group or moiety is of one of the formulas:

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

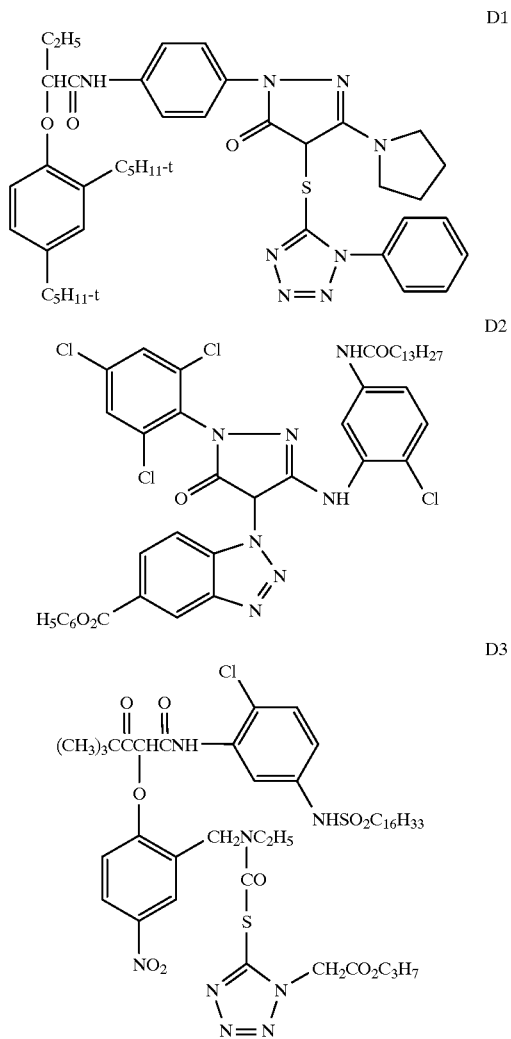

D4
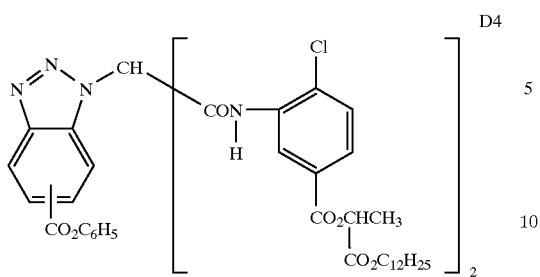
D5
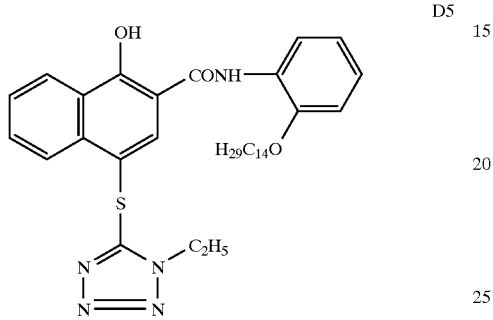
D6
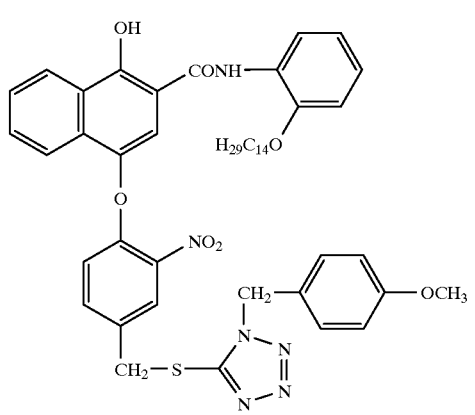
D7
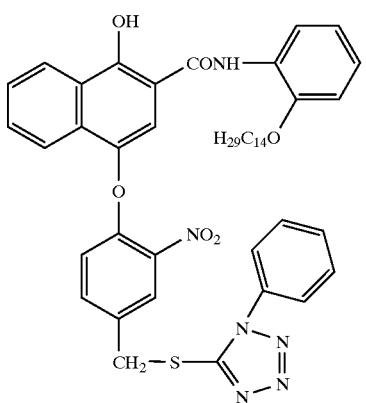
D8
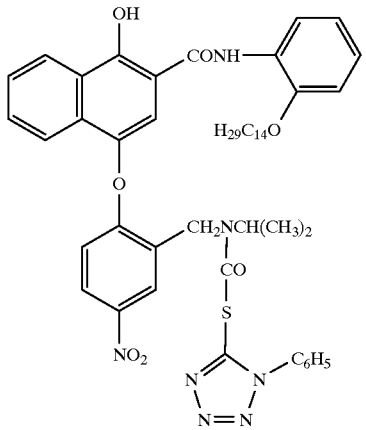
D9
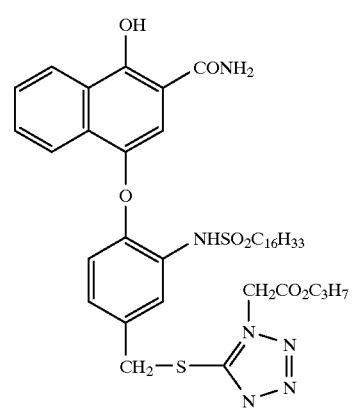
D10
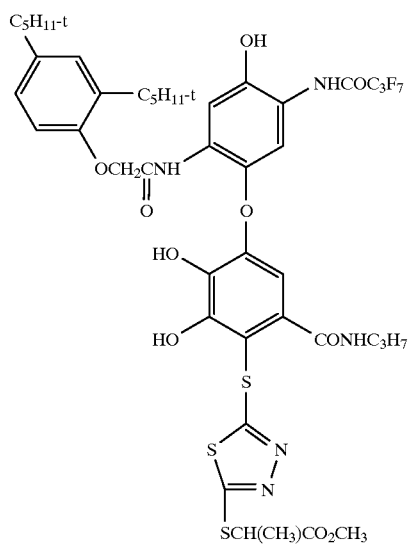

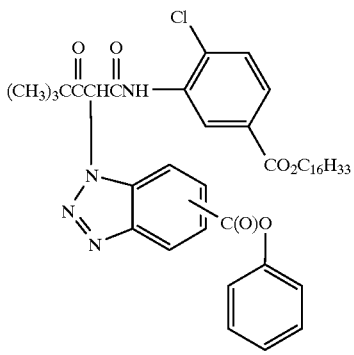

Useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where

ECD is the average equivalent circular diameter of the tabular grains in micrometers and t is the average thickness in micrometers of the tabular grains.

The average useful ECD of photographic emulsions can range up to about 10 micrometers, although in practice emulsion ECD's seldom exceed about 4 micrometers. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micrometer) tabular grains. To achieve the lowest levels of granularity it is preferred that aim tabular grain projected areas be satisfied with ultrathin (t<0.06 micrometer) tabular grains. Tabular grain thicknesses typically range down to about 0.02 micrometer. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micrometer. Ultrathin tabular grain high chloride emulsions are disclosed by Maskasky U.S. Pat. No. 5,217,858.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The emulsions can be surface-sensitive emulsions, i.e., emulsions that form latent images primarily on the surfaces of the silver halide grains, or the emulsions can form internal latent images predominantly in the interior of the silver halide grains. The emulsions are negative-working emulsions, such as surface-sensitive emulsions or unfogged internal latent image-forming emulsions.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. One type of such element is designed for image capture, and speed (the sensitivity of the element to low light conditions) is usually critical to obtaining sufficient image in such elements. When such elements are to be subsequently used to optically generate a color print, they are provided on a transparent support. They may then be processed, for example, in known color negative processes such as the Kodak C-41 process, as described in The British Journal of Photography Annual of 1988, pages 191–198. Kodak ECN-2 process described in the H-24 Manual available from Eastman Kodak Co. may be employed to process motion picture color negative elements. Color negative development times are typically 3' 15" or less and desirably 90 or even 60 seconds or less.

Elements destined for color reflection prints are provided on a reflective support and may be exposed via optical negative/positive printing and processed, for example, using the Kodak RA-4 process as described in The British Journal of Photography Annual of 1988, Pp 198–199; motion picture color projection prints may be processed, for example, in accordance with the Kodak ECP-2 process as described in the H-24 Manual. Reflective color prints are typically provided using silver halide emulsions containing 99% or more of silver chloride, and development times are typically 90 seconds or less and desirably 45 or even 30 seconds or less.

To provide a positive (or reversal) image, the color development step can be preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as the Kodak E-6 process. Alternatively, a direct positive emulsion can be employed to obtain a positive image.

The above types of photographic elements are typically sold with instructions to process using the appropriate method such as the mentioned color negative (Kodak C-41), color print (Kodak RA-4), or reversal (Kodak E-6) process.

Preferred color developing agents are p-phenylenediamines such as: 4-amino-N,N-diethylaniline hydrochloride; 4-amino-3-methyl-N,N-diethylaniline hydrochloride; 4-amino-3-methyl-N-ethyl-N-(2-methanesulfonamidoethyl)aniline sesquisulfate hydrate; 4-amino-3-methyl-N-ethyl-N-(2-hydroxyethyl)aniline sulfate; 4-amino-3-(2-methanesulfonamidoethyl)-N,N-diethylaniline hydrochloride and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The couplers of the invention are readily prepared through conventional techniques. The following will demonstrate a suitable method.

Synthesis of Coupler YC1-X1

Synthesis Scheme

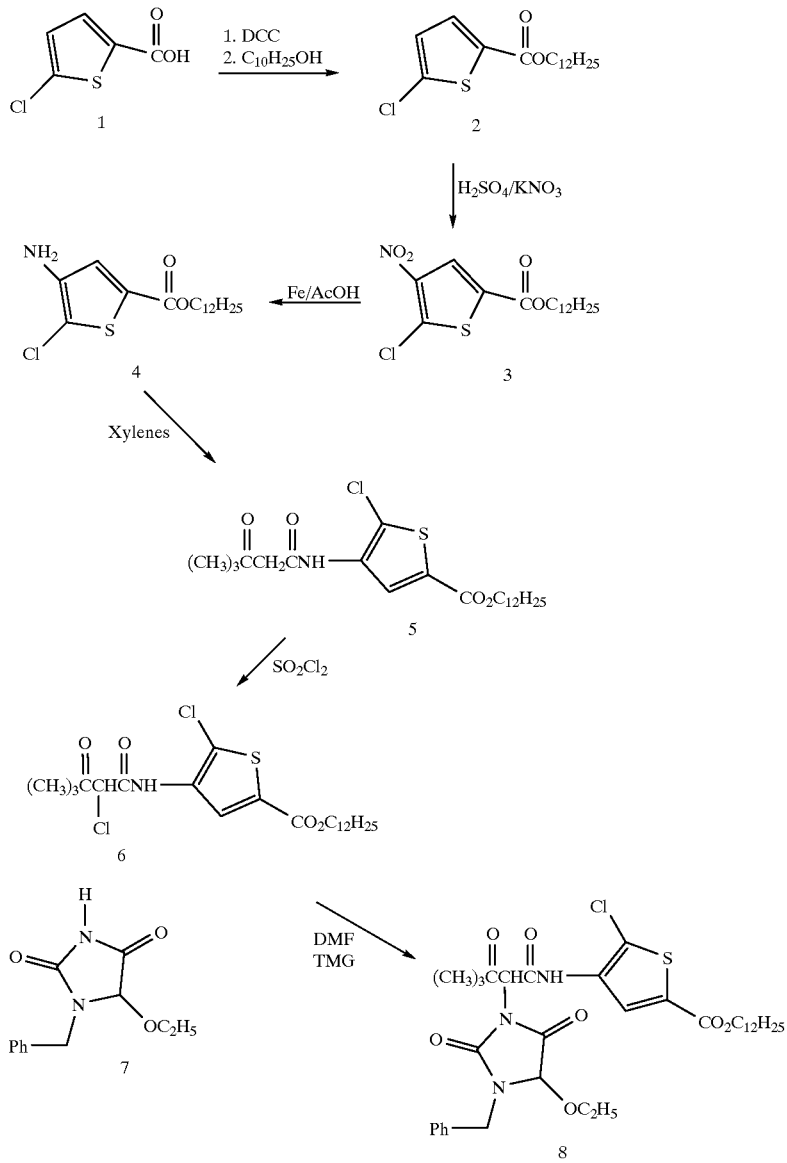

Synthesis of Dodecyl-2-Chloro-Thiophene-5-Carboxylate (Compound 2):

A solution of 15 g (0.09 mol) of 2-Chlorothiophene-5-carboxylic acid 1, 23 mL (0.1 mol) of dodecyl alcohol and a catalytic amount of dimethylaminopyridine (DMAP) in 450 mL of dichloromethane and 100 mL of tetrahydrofuran was stirred at room temperature. 21 g (0.1 mol) of dicyclohexylcarbodiimide (DCC) in 50 mL of dichloromethane was then added in one portion. After stirring at room temperature for 5 minutes, a solid precipitated out of solution. The reaction was stirred for an additional 30 minutes. The solid was removed by filtration and discarded. The solvent was removed under vacuum. The resulting oil was dissolved in ligroins and purified by column chromatography to obtain compound 2, a clear oil, 24.3 g (82%). The structure was confirmed by NMR spectroscopy.

Synthesis of Dodecyl-2-Chloro-3-nitrothiophene-5-Carboxylate (Compound 3):

A solution of 55.5 g (0.17 mol) of 2 in 300 mL sulfuric acid was cooled to 5° C. on an ice/acetone bath. Potassium nitrate (17.8 g, 0.18 mol) in 50 mL of sulfuric acid was added dropwise at a rate sufficient to keep the reaction temperature under 10° C. Thin layer chromatography of the product showed one major spot. The reaction mixture was poured into 1 L of ice water, and then the aqueous mixture was extracted with 1 L of ethyl acetate. The extract was dried over magnesium sulfate, filtered and concentrated under reduced pressure. The resulting oil was crystallized from an isopropyl alcohol/water mixture. After filtration, 28.8 g of 3 was obtained as a pale yellow solid (45% yield). The structure was confirmed by NMR spectroscopy.

Synthesis of Dodecyl-2-Chloro-3-aminothiophene-5-Carboxylate (Compound 4):

A slurry of 28.8 g (0.08 mol) of 3 in 250 mL of glacial acetic acid and 25 mL of water was heated to reflux. The resulting solution was treated portionwise with 22 g (0.4 mol) of iron. The solution was refluxed for 15 minutes. This layer chromatography of the product showed one major spot. The solution was filtered hot through celite. The acetic acid mixture was poured into 2 L of ice water. The solid which precipitated was filtered and air dried. 26.2 g of 4 was obtained as a gray solid (95%).

Synthesis of Compound 5 (Coupler YC1):

A solution of 12.7 g (0.04 mol) of 4 and 11.6 mL (0.08 mol) of methyl-dimethyl-oxovalerate in 250 mL of xylenes was refluxed into a dean stark trap for 4 hours. The solvent was removed under reduced pressure on a Buchi roto evaporator. The oil obtained was purified by column chromatography, eluting with ligroins and 10% ethyl acetate. The fractions containing 5 were concentrated to an oil. The oil was dissolved in isopropyl alcohol, and water was added until the solution was cloudy. On stirring a solid formed, which was collected by filtration the yield was 14.1 g (83%). The structure was confirmed as compound 5 by spectroscopy.

Synthesis of Compound 6:

A solution of 14.1 g (0.03 mol) of 5 in 250 mL of dichloromethane was treated dropwise with 2.4 mL of sulfuryl chloride (0.03 mol) over a 20 minute period. After 4 hours the solvent was removed under reduced pressure. The oil obtained was dissolved in isopropyl alcohol, and water was added until the solution was cloudy. After 30 minutes the oil solidified. The cream colored solid, 6, was collected by filtration. The yield was 14.3 g (94%). The structure was confirmed by NMR spectroscopy.

Synthesis of Compound 8 (Coupler YC1-X1):

A solution of 14.2 g (0.028 mol) of 6 and 6.6 g (0.028 mol) of 7 in 100 mL of dimethylformamide was treated with 3 equivalents of tetramethylguanidine The reaction was warmed to 50° C. for 2 hours. The reaction mixture was cooled to room temperature and then partitioned between 1 liter of ethyl acetate and 1 liter of 10% HCl. The product was extracted into the organic layer. The organic layer was dried with magnesium sulfate. The solvent was removed under reduced pressure on a roto evaporator. The product was purified by column chromatography, eluting with ligroins/ethyl acetate 10%. The yellow oil obtained was dissolved in isopropyl alcohol and water was added until the solution was cloudy. After 1 hour the product solidified. This was filtered to give 6.6 g (33 % yield) of 8 as a white solid. The structure was confirmed by NMR spectroscopy and combustion analysis.

Photographic Examples

A photographic coating of comparative yellow dye-forming coupler A1 was prepared with a silver iodobromide emulsion (3.5% iodide) on a transparent support. The coating structure is shown in Table I, with laydowns in $g/m^2$ given in parentheses. Coupler A1 was coated at a level of 1.076 millimoles/$m^2$ along with dibutyl phthalate coupler solvent at a 1:1 weight ratio. An aqueous dispersion of the coupler was prepared for coating by adding an oil phase containing 1:1:3 weight ratio of coupler:dibutyl phthalate::ethyl acetate to an aqueous phase containing gelatin and the dispersing agent ALKANOL XC (DuPont) in a 1:10 weight ratio. The mixture was then passed through a colloid mill to disperse the oil phase in the aqueous phase as small particles. On coating the ethyl acetate auxiliary solvent evaporates.

TABLE I

Overcoat:
Gelatin (2.69)
Bis(vinylsulfonyl)methane Hardener (0.129)
A1 (Comparative Coupler) (0.751) & dibutyl phthalate (0.751)
0.70 m Silver Iodobromide Emulsion (0.755 Ag)
Gelafin (3.77)
Cellulose Acetate Butyrate Support

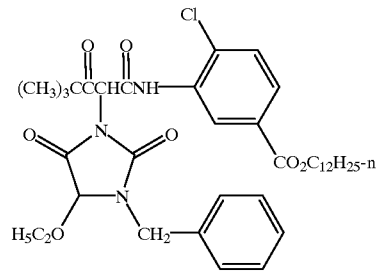

A1

A photographic coating comprising a yellow dye-forming coupler of this invention was similarly prepared by substituting an equimolar amount of coupler YC2-X1 (0.795 $g/m^2$) for coupler A1 with dibutyl phthalate maintained at a 1:1 weight ratio (0.795 $g/m^2$).

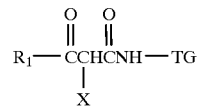

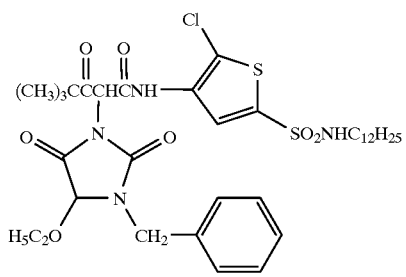

After hardening, the two film samples were exposed and processed with standard C-41 chemicals using the conditions in Table II.

TABLE II

C-41 Processing Solutions And Conditions

| Solution | Process Time | Agitation Gas |
|---|---|---|
| C-41 Developer | 2'00" | Nitrogen |
| Stop Bath | 30" | Nitrogen |
| Wash | 2'00" | None |
| Bleach | 3'00" | Air |
| Wash | 3'00" | None |
| Fix | 4'00" | Nitrogen |
| Wash | 3'00" | None |
| Wetting Agent Bath | 30" | None |

Process temperature 100° F.(37.8° C).

Measurements of photographic contrast (gamma), Status M maximum density (Dmax) and light-induced fade (percent fade from an initial blue density of approximately 1.0 after 6 weeks exposure to 5.4 klux daylight irradiation) were then made on the processed films. As shown in Table III, coupler YC2-X1 of this invention provided desirable increases in both Dmax and gamma and a desirable reduction in percent fade after 6 wk exposure to 5.4 klux daylight irradiation.

TABLE III

| Coating No. | Yellow Imaging Coupler | Dmax | Gamma | % Fade 6 wk, 5.4 klux |
|---|---|---|---|---|
| 1 | A1 (Comparison) | 1.73 | 1.04 | 54 |
| 2 | YC2-X1 (Invention) | 1.92 | 1.28 | 40 |

In a similar comparison, the dye formed from coupler YC1-X1 in a processed film showed 13% less fade than the dye formed from comparison coupler A1 after one week irradiation at 50 klux through a Wratten 2C filter.

The entire contents of all copending applications, patents, and other publications cited in this specification are incorporated herein by reference. While there has been shown and described what are presently considered to be the preferred embodiments of the invention, various modifications and alterations will be obvious to those skilled in the art. All such modifications and alterations are intended to fall within the scope of the appended claims.

What is claimed is:

1. A photographic element comprising a silver halide emulsion layer having associated therewith a dye-forming coupler represented by Formula I:

$$R_1-\text{CCHCNH}-TG$$
$$\quad\quad\ \ |$$
$$\quad\quad\ \ X$$

wherein $R_1$ is a tertiary alkyl group, an aryl group, an anilino group, an alkylamino group, an arylamino group or a heterocyclic group; TG is a thiophene group; and X is hydrogen or a coupling-off group.

2. The photographic element of claim 1, wherein $R_1$ is a tertiary alkyl group.

3. The photographic element of claim 1, wherein TG is a substituted thiophene group wherein at least one substituent is a halogen atom or an alkoxy or aryloxy group.

4. The photographic element of claim 1, wherein TG is a thiophene group having a ballasting group substituent containing at least 5 carbon atoms.

5. The photographic element of claim 1, wherein the dye-forming coupler is of Formula II:

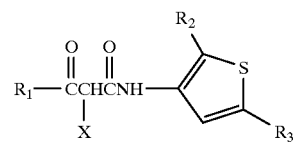

wherein $R_1$ and X are as defined in claim 1, $R_2$ is an alkoxy or aryloxy group or a halogen atom, and $R_3$ is an electron withdrawing group.

6. The photographic element of claim 5, wherein $R_3$ comprises a group having a Hammett $\sigma_p$ constant of greater than 0.1.

7. The photographic element of claim 5, wherein $R_3$ comprises a group having a Hammett $\sigma_p$ constant of greater than 0.3.

8. The photographic element of claim 5, wherein $R_3$ comprises a cyano group, a nitro group, a substituted or unsubstituted carbamoyl group having from 1 to 30 carbon atoms, a substituted or unsubstituted sulfamoyl group having from 1 to 30 carbon atoms, a substituted or unsubstituted alkoxycarbonyl group having from 1 to 30 carbon atoms, a substituted or unsubstituted sulfonyl group having from 1 to 30 carbon atoms, a substituted or unsubstituted acyloxy group having from 1 to 30 carbon atoms, a trifluoromethyl group, a carboxyl group, or a substituted or unsubstituted heterocyclic residue group having from 1 to 30 carbon atoms.

9. The photographic element of claim 5, wherein $R_3$ comprises a sulfamoyl group, a carbamoyl group or a sulfonyl group.

10. The photographic element of claim 5, wherein $R_1$ is a tertiary alkyl group.

11. The photographic element of claim 5, wherein at least one of $R_2$ and $R_3$ comprises a ballasting group substituent containing at least 5 carbon atoms.

12. The element of claim 1 wherein the dye-forming coupler of is selected from the group consisting of:

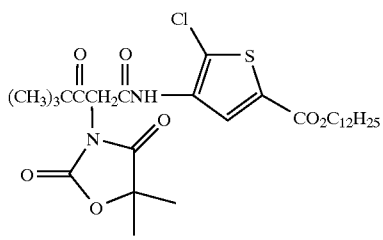
YC1-X2

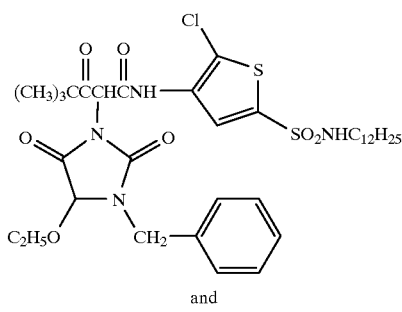
YC2-X1 and

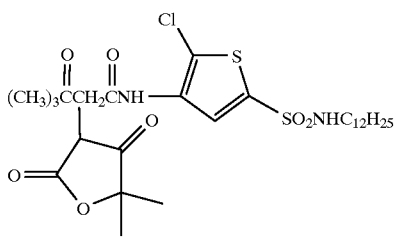
YC2-X2

13. A process for forming an image in an element as described in claim 1 after the element has been imagewise exposed to light comprising contacting the exposed element with a color photographic developer solution, and reacting the dye-forming coupler with oxidized color developer to form an image dye.

14. The photographic element of claim 2, wherein TG is a substituted thiophene group wherein at least one substituent is a halogen atom or an alkoxy or aryloxy group.

15. The photographic element of claim 2, wherein TG is a thiophene group having a ballasting group substituent containing at least 5 carbon atoms.

16. The photographic element of claim 10, wherein $R_3$ comprises a group having a Hammett $\sigma_p$ constant of greater than 0.1.

17. The photographic element of claim 10, wherein $R_3$ comprises a group having a Hammett $\sigma_p$ constant of greater than 0.3.

18. The photographic element of claim 10, wherein $R_3$ comprises a cyano group, a nitro group, a substituted or unsubstituted carbamoyl group having from 1 to 30 carbon atoms, a substituted or unsubstituted sulfamoyl group having from 1 to 30 carbon atoms, a substituted or unsubstituted alkoxycarbonyl group having from 1 to 30 carbon atoms, a substituted or unsubstituted sulfonyl group having from 1 to 30 carbon atoms, a substituted or unsubstituted acyloxy group having from 1 to 30 carbon atoms, a trifluoromethyl group, a carboxyl group, or a substituted or unsubstituted heterocyclic residue group having from 1 to 30 carbon atoms.

19. The photographic element of claim 10, wherein $R_3$ comprises a sulfamoyl group, a carbamoyl group or a sulfonyl group.

20. The photographic element of claim 10, wherein at least one of $R_2$ and $R_3$ comprises a ballasting group substituent containing at least 5 carbon atoms.

* * * * *